(12) United States Patent
Sheremet'eva et al.

(10) Patent No.: US 7,381,548 B2
(45) Date of Patent: Jun. 3, 2008

(54) **METHOD FOR PRODUCING L-AMINO ACID USING BACTERIUM OF *ENTEROBACTERIACEAE* FAMILY HAVING EXPRESSION OF *YAFA* GENE ATTENUATED**

(75) Inventors: Marina Evgenievna Sheremet'eva, Moscow (RU); Konstantin Vyacheslavovich Rybak, Moscow (RU); Tatyana Viktorovna Leonova, Moscow (RU); Elvira Borisovna Voroshilova, Moscow (RU); Yury Ivanovich Kozlov, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 145 days.

(21) Appl. No.: 11/298,609

(22) Filed: Dec. 12, 2005

(65) Prior Publication Data

US 2006/0286643 A1    Dec. 21, 2006

Related U.S. Application Data

(60) Provisional application No. 60/693,509, filed on Jun. 24, 2005.

(30) Foreign Application Priority Data

Dec. 21, 2004 (RU) ............................. 2004137198

(51) Int. Cl.
*C12P 13/04* (2006.01)
*C12P 13/22* (2006.01)
*C12P 13/08* (2006.01)
*C12N 9/00* (2006.01)
*C12N 15/74* (2006.01)
*C07H 21/02* (2006.01)
*C07K 1/00* (2006.01)

(52) U.S. Cl. .................. 435/106; 435/108; 435/115; 435/183; 435/252.3; 435/488; 536/23.1; 530/350

(58) Field of Classification Search ............... 435/106, 435/108, 115, 183, 252.3, 488; 536/23.1; 530/350

See application file for complete search history.

(56) References Cited

U.S. PATENT DOCUMENTS

| | | | |
|---|---|---|---|
| 6,960,455 | B2 | 11/2005 | Livshits et al. |
| 2004/0038380 | A1 | 2/2004 | Debabov et al. |
| 2004/0132165 | A1 | 7/2004 | Akhverdian et al. |
| 2004/0229320 | A1 | 11/2004 | Stoynova et al. |
| 2004/0229321 | A1 | 11/2004 | Savrasova et al. |
| 2005/0048631 | A1 | 3/2005 | Klyachko et al. |
| 2005/0054061 | A1 | 3/2005 | Klyachko et al. |
| 2005/0124048 | A1 | 6/2005 | Akhverdian et al. |
| 2005/0176033 | A1 | 8/2005 | Klyachko et al. |
| 2005/0214911 | A1 | 9/2005 | Marchenko et al. |
| 2005/0214913 | A1 | 9/2005 | Marchenko et al. |
| 2005/0239175 | A1 | 10/2005 | Tabolina et al. |

FOREIGN PATENT DOCUMENTS

| | | |
|---|---|---|
| EP | 0864654 | 9/1998 |
| WO | WO94/08031 | 4/1994 |

OTHER PUBLICATIONS

Koo et al. J. Biol. Chem. Jul. 23, 2004;279(30):31613-21. Epub May 28, 2004.*
International Preliminary Report on Patentability for PCT Patent App. No. PCT/JP2005/023830 (Jul. 5, 2007).
Nüesch, J., et al., "Structural and functional organization of the *gpt* gene region of *Escherichia coli*," Gene 1984;32:243-249.
International Search Report and Written Opinion of the International Searching Authority for PCT App. No. PCT/JP2005/023830 (May 10, 2006).
Datsenko, K. A., et al., "One-step inactivation of chromosomal genes in *Escherichia coli* K-12 using PCR products," PNAS 2000;97(12):6640-6645.
Koo, B-Y, et al., "A Novel Fermentation/Respiration Switch Protein Regulated by Enzyme IIA$^{Glc}$ in *Escherichia coli*," J. Biol. Chem. 2004;279(30):31613-31621.
Postma, P.W., et al., "Phosphoenolpyruvate: Carbohydrate Phosphotransferase Systems," *Escherichia coli* and *Salmonella*, Second Edition, Editor in Chief: F. C. Neidhardt, ASM Press, Washington, D.C., 1996, pp. 1149-1174.
Yu, D., et al., "An efficient recombination system for chromosome engineering in *Escherichia coli*," PNAS 2000;97(11):5978-5983.
U.S. Appl. No. 09/684,618, filed Oct. 10, 2000, Gusyatiner et al.
U.S. Appl. No. 60/586,222, filed Jul. 9, 2004, Akhverdian et al.
U.S. Appl. No. 60/587,492, filed Jul. 14, 2004, Klyachko et al.
U.S. Appl. No. 60/610,545, filed Sep. 17, 2004, Marchenko et al.
U.S. Appl. No. 60/644,562, filed Jan. 19, 2005, Rybak et al.
U.S. Appl. No. 60/673,807, filed Apr. 22, 2005, Rybak et al.
U.S. Appl. No. 60/693,507, filed Jun. 24, 2005, Rybak et al.
U.S. Appl. No. 60/693,509, filed Jun. 24, 2005, Sheremet'eva et al.
U.S. Appl. No. 60/703,414, filed Jul. 29, 2005, Ptitsyn et al.
U.S. Appl. No. 60/703,426, filed Jul. 29, 2005, Rybak et al.
U.S. Appl. No. 60/703,444, filed Jul. 29, 2005, Rybak et al.
U.S. Appl. No. 11/200,296, filed Aug. 10, 2005, Kozlov et al.
U.S. Appl. No. 11/204,011, filed Aug. 16, 2005, Livshits et al.
U.S. Appl. No. 60/714,843, filed Sep. 8, 2005, Filippov et al.
U.S. Appl. No. 60/714,844, filed Sep. 8, 2005, Filippov et al.
U.S. Appl. No. 60/714,848, filed Sep. 8, 2005, Filippov et al.
U.S. Appl. No. 60/714,849, filed Sep. 8, 2005, Filippov et al.
U.S. Appl. No. 60/714,850, filed Sep. 8, 2005, Gulevich et al.
U.S. Appl. No. 11/220,669, filed Sep. 8, 2005, Savrasova et al.
U.S. Appl. No. 60/723,566, filed Oct. 5, 2005, Rybak et al.
U.S. Appl. No. 60/723,923, filed Oct. 6, 2005, Filippov et al.
U.S. Appl. No. 60/723,924, filed Oct. 6, 2005, Rybak et al.

(Continued)

Primary Examiner—Tekchand Saidha
Assistant Examiner—Christian L Fronda
(74) Attorney, Agent, or Firm—Shelly Guest Cermak; Cermak Kenealy & Vaidya LLP (57) ABSTRACT

The present invention provides a method for producing an L-amino acid using a bacterium of the Enterobacteriaceae family, particularly a bacterium belonging to genus *Escherichia* or *Pantoea*, which has been modified to attenuate expression of the yafA gene.

2 Claims, 3 Drawing Sheets

OTHER PUBLICATIONS

U.S. Appl. No. 60/723,925, filed Oct. 6, 2005, Rybak et al.
U.S. Appl. No. 60/723,928, filed Oct. 6, 2005, Rybak et al.
U.S. Appl. No. 60/723,929, filed Oct. 6, 2005, Filippov et al.
U.S. Appl. No. 11/247,138, filed Oct. 12, 2005, Rybak et al.
U.S. Appl. No. 60/736,830, filed Nov. 16, 2005, Filippov et al.
U.S. Appl. No. 60/736,867, filed Nov. 16, 2005, Altman et al.
U.S. Appl. No. 11/275,264, filed Dec. 21, 2005, Rybak et al.
U.S. Appl. No. 11/275,507, filed Jan. 11, 2006, Ptitsyn et al.
U.S. Appl. No. 11/275,569, filed Jan. 17, 2006, Rybak et al.
U.S. Appl. No. 60/743,222, filed Feb. 3, 2006, Rybak et al.
U.S. Appl. No. 60/743,223, filed Feb. 3, 2006, Rybak et al.
U.S. Appl. No. 60/743,226, filed Feb. 3, 2006, Rybak et al.

* cited by examiner

Fig. 1

Obtained PCR product (965 bp)

METHOD FOR PRODUCING L-AMINO ACID USING BACTERIUM OF *ENTEROBACTERIACEAE* FAMILY HAVING EXPRESSION OF *YAFA* GENE ATTENUATED

This application claims priority under 35 U.S.C. §119(a) to Russian patent application 2004137198, filed Dec. 21, 2004, and under 35 U.S.C. §119(e) to U.S. provisional patent application 60/693,509, filed on Jun. 24, 2005, the entireties of both are hereby incorporated by reference. Also, the Sequence Listing on compact disk filed herewith is hereby incorporated by reference (File name: US-194 Seq List; File size: 12 KB; Date recorded: Dec. 12, 2005).

BACKGROUND OF THE INVENTION

1. Field of the Invention

The present invention relates to the microbiological industry, and specifically to a method for producing an L-amino acid using a bacterium of the *Enterobacteriaceae* family which has been modified to attenuate expression of the yafA gene.

2. Brief Description of the Related Art

The bacterial phosphoenolpyruvate (PEP):sugar phosphotransferase system (PTS) plays an important role in the transport of a variety of sugar substrates. The PTS of *Escherichia coli* is composed of two general cytoplasmic proteins, enzyme I (EI) and histidine phosphocarrier protein, HPr, which are used for all sugars, and some sugar-specific components collectively known as enzymes II, comprising soluble enzyme $IIA^{Glc}$ and membrane bound enzyme $IICB^{Glc}$ (*Escherichia coli* and *Salmonella*, Second Edition, Editor in Chief: F. C. Neidhardt, ASM Press, Washington D.C., 1996, pp. 1149-1174). Glucose uptake entails sequential phosphoryl transfer via the PTS, as follows: phosphoenolpyruvate (PEP) →EI→HPr→$IIA^{Glc}$→$IICB^{Glc}$→glucose.

Each protein component of the *E. coli* PTS involved in glucose uptake has been shown to regulate the activity of a partner protein via direct protein-protein interaction. These regulatory functions of PTS depend on the phosphorylation state of the involved component. The err gene product (enzyme $IIA^{Glc}$) mediates some of these regulatory phenomena. The product of the yafA (also known as frsA) gene, FrsA (fermentation/respiration switch protein) regulator protein was shown to form a complex which specifically interacts with the unphosphorylated form of $IIA^{Glc}$ (Koo, B. M. et al. J Biol Chem. Jul. 23, 2004; 279(30): 31613-21). The authors also reported that disruption of the yafA gene increased cellular respiration on several sugars including glucose.

Currently, there have been no reports of inactivating the yafA gene for production of L-amino acids.

SUMMARY OF THE INVENTION

Objects of the present invention include enhancing the productivity of L-amino acid-producing strains and providing a method for producing an L-amino acid using these strains.

The above objects were achieved by finding that attenuating the expression of the yafA gene can enhance production of L-amino acids, such as L-threonine, L-lysine, L-cysteine, L-leucine, L-histidine, L-glutamic acid, L-phenylalanine, L-tryptophan, L-proline, and L-arginine.

The present invention provides a bacterium of the *Enterobacteriaceae* family having an increased ability to produce amino acids, such as L-threonine, L-lysine, L-cysteine, L-leucine, L-histidine, L-glutamic acid, L-phenylalanine, L-tryptophan, L-proline, and L-arginine.

It is an object of the present invention to provide an L-amino acid-producing bacterium of the *Enterobacteriaceae* family, wherein the bacterium has been modified to attenuate expression of the yafA gene.

It is a further object of the present invention to provide the bacterium as described above, wherein the expression of the yafA gene is attenuated by inactivation of the yafA gene.

It is a further object of the present invention to provide the bacterium as described above, wherein the bacterium belongs to the genus *Escherichia*.

It is a further object of the present invention to provide the bacterium as described above, wherein the bacterium belongs to the genus *Pantoea*.

It is a further object of the present invention to provide the bacterium as described above, wherein said L-amino acid is selected from the group consisting of an aromatic L-amino acid and a non-aromatic L-amino acid.

It is a further object of the present invention to provide the bacterium as described above, wherein said aromatic L-amino acid is selected from the group consisting of L-phenylalanine, L-tyrosine, and L-tryptophan.

It is a further object of the present invention to provide the bacterium as described above, wherein said non-aromatic L-amino acid is selected from the group consisting of L-threonine, L-lysine, L-cysteine, L-methionine, L-leucine, L-isoleucine, L-valine, L-histidine, L-glycine, L-serine, L-alanine, L-asparagine, L-aspartic acid, L-glutamine, L-glutamic acid, L-proline, and L-arginine.

It is a further object of the present invention to provide a method for producing an L-amino acid comprising:
   cultivating the bacterium as described above in a medium to produce and excrete said L-amino acid into the medium, and
   collecting said L-amino acid from the medium.

It is a further object of the present invention to provide the method as described above, wherein said L-amino acid is selected from the group consisting of an aromatic L-amino acid and a non-aromatic L-amino acid.

It is a further object of the present invention to provide the method as described above, wherein said aromatic L-amino acid is selected from the group consisting of L-phenylalanine, L-tyrosine, and L-tryptophan.

It is a further object of the present invention to provide the method as described above, wherein said non-aromatic L-amino acid is selected from the group consisting of L-threonine, L-lysine, L-cysteine, L-methionine, L-leucine, L-isoleucine, L-valine, L-histidine, L-glycine, L-serine, L-alanine, L-asparagine, L-aspartic acid, L-glutamine, L-glutamic acid, L-proline, and L-arginine.

The present invention is described in detail below.

DESCRIPTION OF THE PREFERRED EMBODIMENTS

1. Bacterium of the Present Invention

The bacterium of the present invention is an L-amino acid-producing bacterium of the *Enterobacteriaceae* family, wherein the bacterium has been modified to attenuate expression of the yafA gene.

In the present invention, "L-amino acid-producing bacterium" means a bacterium which has an ability to produce and excrete an L-amino acid into a medium, when the bacterium is cultured in the medium.

The term "L-amino acid-producing bacterium" as used herein also means a bacterium which is able to produce and cause accumulation of an L-amino acid in a culture medium in an amount larger than a wild-type or parental strain of *E. coli*, such as *E. coli* K-12, and preferably means that the microorganism is able to cause accumulation in a medium of an amount not less than 0.5 g/L, more preferably not less than 1.0 g/L, of the target L-amino acid. The term "L-amino acid" includes L-alanine, L-arginine, L-asparagine, L-aspartic acid, L-cysteine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, and L-valine.

The term "aromatic L-amino acid" includes L-phenylalanine, L-tyrosine, and L-tryptophan. The term "non-aromatic L-amino acid" includes L-threonine, L-lysine, L-cysteine, L-methionine, L-leucine, L-isoleucine, L-valine, L-histidine, L-glycine, L-serine, L-alanine, L-asparagine, L-aspartic acid, L-glutamine, L-glutamic acid, L-proline, and L-arginine. L-threonine, L-lysine, L-cysteine, L-leucine, L-histidine, L-glutamic acid, L-phenylalanine, L-tryptophan, L-proline, and L-arginine are particularly preferred.

The *Enterobacteriaceae* family includes bacteria belonging to the genera *Escherichia*, *Enterobacter*, *Erwinia*, *Klebsiella*, *Pantoea*, *Photorhabdus*, *Providencia*, *Salmonella*, *Serratia*, *Shigella*, *Morganella*, *Yersinia*, etc. Specifically, those classified into the *Enterobacteriaceae* according to the taxonomy used by the NCBI (National Center for Biotechnology Information) database (http://www.ncbi.nlm.nih.gov/htbinpost/Taxonomy/wgetorg ? mode = Tree & id = 1236 &lvl =3&keep=1&srchmode=1&unlock) can be used. A bacterium belonging to the genus *Escherichia* or *Pantoea* is preferred.

The phrase "a bacterium belonging to the genus *Escherichia*" means that the bacterium is classified into the genus *Escherichia* according to the classification known to a person skilled in the art of microbiology. Examples of a bacterium belonging to the genus *Escherichia* as used in the present invention include, but are not limited to, *Escherichia coli* (*E. coli*).

The bacterium belonging to the genus *Escherichia* that can be used in the present invention is not particularly limited; however, e.g., bacteria described by Neidhardt, F. C. et al. (*Escherichia coli* and *Salmonella typhimurium*, American Society for Microbiology, Washington D.C., 1208, Table 1) are encompassed by the present invention.

The phrase "a bacterium belonging to the genus *Pantoea*" means that the bacterium is classified into the genus *Pantoea* according to the classification known to a person skilled in the art of microbiology. Some species of *Enterobacter agglomerans* have been recently re-classified into *Pantoea agglomerans*, *Pantoea ananatis*, *Pantoea stewartii* or the like, based on the nucleotide sequence analysis of 16S rRNA, etc. (Int. J. Syst. Bacteriol., 43, 162-173 (1993)).

The phrase "bacterium has been modified to attenuate expression of the yafA gene" means that the bacterium has been modified in such a way that the modified bacterium contains a reduced amount of the FrsA protein, as compared with an unmodified bacterium, or is unable to synthesize the FrsA protein.

The phrase "inactivation of the yafA gene" means that the modified gene encodes a completely non-functional protein. It is also possible that the modified DNA region is unable to naturally express the gene due to the deletion of a part of the gene, the shifting of the reading frame of the gene, the introduction of missense/nonsense mutation(s), or the modification of an adjacent region of the gene, including sequences controlling gene expression, such as promoters, enhancers, attenuators, ribosome-binding sites, etc.

The role of the FrsA regulator protein encoded by the yafA gene in L-amino acid production remains unclear. But it has been shown that disruption of the yafA gene results in an increase of cellular respiration on several sugars, including glucose (Koo, B. M. et al. J Biol Chem. Jul. 23, 2004;279(30):31613-21).

The yafA gene encodes the FrsA regulator protein, which forms 1:1 complex specifically with the unphosphorylated form of $IIA^{Glc}$. The yafA gene of *E. coli* (gi:16128225; numbers 256527 to 257771 in the GenBank accession number NC_000913.1) is located between the gpt and crl genes on the chromosome of *E. coli* K-12. The nucleotide sequence of the yafA gene and the amino acid sequence of the FrsA regulator protein encoded thereby are shown in SEQ ID NO:3 and SEQ ID NO:4, respectively.

A BLAST search revealed that orthologs of FrsA exist only in some gram-negative bacteria, such as *E. coli*, *Salmonella typhimurium*, *Shigella flexneri*, *Yersinia pestis*, *Vibrio cholerae*, *V. vulnificus*, *V. parahaemolyticus* and *Photorhabdus luminescens* (www.ncbi.nlm.nih.gov). All of these species are facultative anaerobes belonging to the γ-proteobacterial group and most of them are highly pathogenic.

A model of the transmembrane topology for the FrsA protein was generated (FIG. 3) based on the statistical analysis of TMbase, a database of naturally occurring transmembrane proteins. The TMpred program predicts membrane-spanning regions and their orientation. The prediction is made using a combination of several weight-matrices for scoring (TMbase—A database of membrane spanning proteins segments. K. Hofmann & W. Stoffel (1993) Biol. Chem. Hoppe-Seyler, 374, 166, www.ch.embnet.org/software/TMPRED_form.html). The model revealed 6 strong transmembrane helices with a total score of 6482 with prediction parameters: TM-helix length between 14 and 35.

Figure 3:
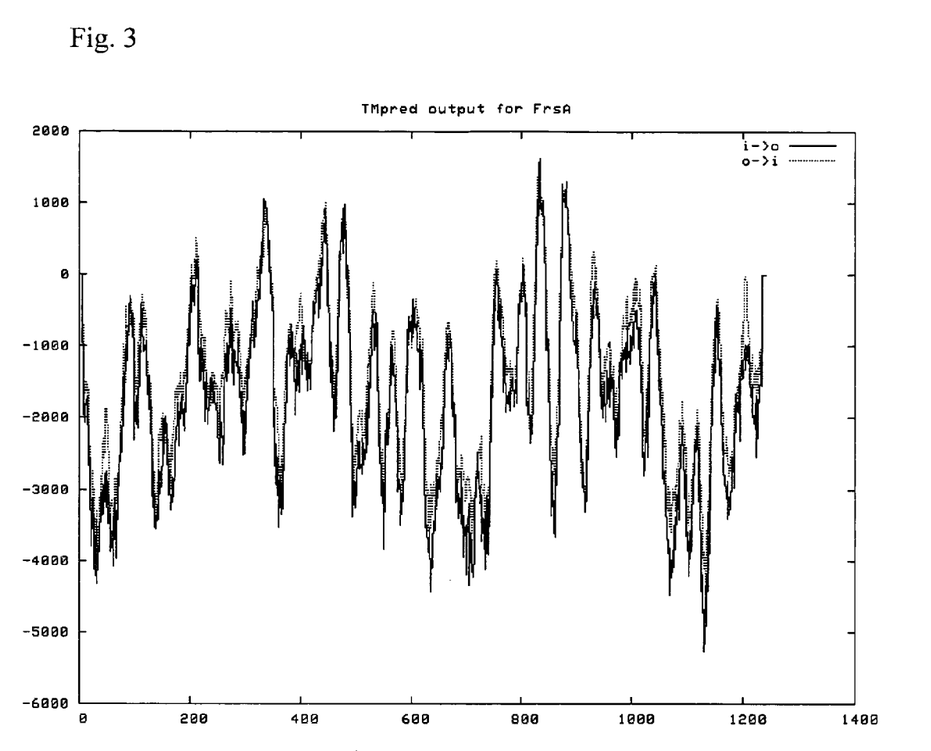
FIG. 3 shows the model for transmembrane topology for the FrsA protein, based on the statistical analysis of the TMbase.

| # | from | to | length | score | orientation |
|---|------|-----|--------|-------|-------------|
| 1 | 205 | 223 | (19) | 513 | o-i (outside-inside) |
| 2 | 328 | 346 | (19) | 1059 | i-o |
| 3 | 435 | 454 | (20) | 1016 | o-i |
| 4 | 472 | 487 | (16) | 980 | i-o |
| 5 | 823 | 841 | (19) | 1604 | o-i |
| 6 | 871 | 890 | (20) | 1310 | i-o |

Since there may be some differences in DNA sequences between the genera or strains of the *Enterobacteriaceae* family, the yafA gene to be inactivated on the chromosome is not limited to the gene shown in SEQ ID No: 1, but may include genes homologous to SEQ ID No: 1 encoding a variant protein of the FrsA protein. The phrase "variant protein" as used in the present invention means a protein which has changes in the sequence, whether they are deletions, insertions, additions, or substitutions of amino acids, but still maintains the activity of the product as the FrsA regulator protein. The number of changes in the variant protein depends on the position or the type of amino acid residues in the three dimensional structure of the protein. It may be 2 to 30, preferably 2 to 15, and more preferably 2 to 5 in SEQ ID NO: 2. These changes in the variants can occur in regions of the protein which are not critical for the function of the protein. This is because some amino acids have high homology to one another so the three dimensional structure or activity is not affected by such a change. These changes in the variant protein can occur in regions of the protein which are not critical for the function of the protein. Therefore, the protein variant encoded by the yafA gene may have a homology of not less than 80%, preferably not less than 90%, and most preferably not less than 95%, with respect to the entire amino acid sequence shown in SEQ ID NO. 2, as long as the activity of the product as the FrsA regulator protein is maintained.

Homology between two amino acid sequences can be determined using the well-known methods, for example, the computer program BLAST 2.0, which calculates three parameters: score, identity and similarity. Moreover, the yafA gene may be a variant which hybridizes under stringent conditions with the nucleotide sequence shown in SEQ ID NO: 1, or a probe which can be prepared from the nucleotide sequence, provided that it encodes a functional FrsA protein prior to inactivation. "Stringent conditions" include those under which a specific hybrid is formed and a non-specific hybrid is not formed. For example, stringent conditions are exemplified by washing one time or more, preferably two or three times, at a salt concentration of 1×SSC, 0.1% SDS, preferably 0.1×SSC, 0.1% SDS, at 60° C. Duration of washing depends on the type of membrane used for blotting and, as a rule, should be what is recommended by the manufacturer. For example, the recommended duration of washing for the Hybond™ N+ nylon membrane (Amersham) under stringent conditions is 15 minutes. Preferably, washing may be performed 2 to 3 times. The length of the probe may be suitably selected, depending on the hybridization conditions, and usually varies from 100 bp to 1 kbp.

Inactivation of the gene can be performed by conventional methods, such as mutagenesis treatment using UV irradiation or nitrosoguanidine (N-methyl-N'-nitro-N-nitrosoguanidine) treatment, site-directed mutagenesis, gene disruption using homologous recombination, or/and insertion-deletion mutagenesis (Yu, D. et al., Proc. Nati. Acad. Sci. USA, 2000, 97:12: 5978-83 and Datsenko, K. A. and Wanner, B. L., Proc. Natl. Acad. Sci. USA, 2000, 97:12: 6640-45) also called "Red-driven integration".

The inactivation of the yafA gene can be detected using Phenotype Microarrays (PMs) (Biolog, Inc.) with cell respiration as a reporter system. The assay chemistry uses a tetrazolium dye to calorimetrically detect the respiration of cells. Detailed information about PM experiments is available at www.biolog.com. The Phenotype Microarrays analysis indicates that disruption of the yafA gene increases cell respiration rate on several sugars, including arabinose, fructose, lactose and glucose (Koo, B. M. et al. J Biol Chem. Jul. 23, 2004; 279(30): 31613-21).

The reduced or absent activity of the FrsA protein in the bacterium according to the present invention can be determined when compared to the parent unmodified bacterium. In addition, the level of gene expression can be estimated by measuring the amount of mRNA transcribed from the gene using various well-known methods, including Northern blotting, quantitative RT-PCR, and the like. Amount or molecular weight of the protein encoded by the gene can be measured by well-known methods, including SDS-PAGE followed by immunoblotting assay (Western blotting analysis), and the like.

Methods for preparation of plasmid DNA, digestion and ligation of DNA, transformation, selection of an oligonucleotide as a primer, and the like may be ordinary methods well-known to one skilled in the art. These methods are described, for instance, in Sambrook, J., Fritsch, E. F., and Maniatis, T., "Molecular Cloning: A Laboratory Manual, Second Edition", Cold Spring Harbor Laboratory Press (1989).

L-amino acid-producing bacteria

As a bacterium of the present invention which is modified to attenuate expression of the yafA gene, bacteria which are able to produce either aromatic or non-aromatic L-amino acids may be used.

The bacterium of the present invention can be obtained by attenuating the expression of the yafA gene in a bacterium which inherently has the ability to produce L-amino acids. Alternatively, the bacterium of present invention can be obtained by imparting the ability to produce L-amino acids to a bacterium already having attenuated expression of the yafA gene.

L-threonine-producing bacteria

Examples of parent strains which can be used for deriving the L-threonine-producing bacteria of the present invention include, but are not limited to, strains belonging to the genus *Escherichia*, such as *E. coli* TDH-6/pVIC40 (VKPM B-3996) (U.S. Pat. Nos. 5,175,107 and 5,705,371), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 1978, 14: 947-956), *E. coli* VL643 and VL2055 (EP 1149911 A), and the like.

The strain TDH-6 is deficient in the thrC gene, as well as being sucrose-assimilative, and the ilvA gene has a leaky mutation. This strain also has a mutation in the rhtA gene, which imparts resistance to high concentrations of threonine or homoserine. The strain B-3996 contains the plasmid pVIC40 which was obtained by inserting into a RSF1010-derived vector a thrA*BC operon which includes a mutant thrA gene. This mutant thrA gene encodes aspartokinase homoserine dehydrogenase I which has substantially desensitized feedback inhibition by threonine. The strain B-3996 was deposited in the All-Union Scientific Center of Antibiotics (Nagatinskaya Street 3-A, 117105 Moscow, Russian Federation) on Nov. 19, 1987 under accession number RIA 1867. The strain was also deposited in the Russian National Collection of Industrial Microorganisms (VKPM; Dorozhny proezd. 1, Moscow 117545, Russian Federation) on Apr. 7, 1987 under accession number B-3996. Preferably, the bacterium of the present invention is additionally modified to enhance expression of one or more of the following genes:

the mutant thrA gene which encodes aspartokinase homoserine dehydrogenase I resistant to feedback inhibition by threonine;

the thrB gene which encodes homoserine kinase;

the thrC gene which encodes threonine synthase;

the rhtA gene which encodes a putative transmembrane protein;

the asd gene which encodes aspartate-β-semialdehyde dehydrogenase; and the aspC gene which encodes aspartate aminotransferase (aspartate transaminase);

The thrA gene which encodes aspartokinase homoserine dehydrogenase I of *Escherichia coli* has been elucidated (nucleotide positions 337 to 2799, GenBank accession no. NC_000913.2, gi: 49175990). The thrA gene is located between the thrL and thrB genes on the chromosome of *E. coli* K-12. The thrB gene which encodes homoserine kinase of *Escherichia coli* has been elucidated (nucleotide positions 2801 to 3733, GenBank accession no. NC_000913.2, gi: 49175990). The thrB gene is located between thrA and thrC genes on the chromosome of *E. coli* K-12. The thrC gene which encodes threonine synthase of *Escherichia coli* has been elucidated (nucleotide positions 3734 to 5020, GenBank accession no. NC_000913.2, gi: 49175990). The thrC gene is located between the thrB gene and the yaaX open reading frame on the chromosome of *E. coli* K-12. All three genes function as a single threonine operon.

A mutant thrA gene which encodes aspartokinase homoserine dehydrogenase I resistant to feedback inhibition by threonine, as well as the thrB and thrC genes, can be obtained as one operon from the well-known plasmid pVIC40 which is present in the threonine producing *E. coli* VKPM B-3996. Plasmid pVIC40 is described in detail in U.S. Pat. No. 5,705,371.

The rhtA gene exists at 18 min on the *E. coli* chromosome close to the glnHPQ operon, which encodes components of the glutamine transport system. The rhtA gene is identical to ORF1 (ybiF gene, positions 764 to 1651, GenBank accession no. AAA218541, gi:440181) and located between the pexB and ompX genes. The unit expressing a protein encoded by the ORF1 has been designated the rhtA gene (rht: resistance to homoserine and threonine). Also, it was revealed that the rhtA23 mutation is an A-for-G substitution at position -1 with respect to the ATG start codon (ABSTRACTS of the 17$^{th}$ International Congress of Biochemistry and Molecular Biology in conjugation with the Annual Meeting of the American Society for Biochemistry and Molecular Biology, San Francisco, Calif., Aug. 24-29, 1997, abstract No. 457, EP 1013765 A).

The asd gene of *E. coli* has already been elucidated (nucleotide positions 3572511 to 3571408, GenBank accession no. NC_000913.1, gi:16131307), and can be obtained by PCR (polymerase chain reaction; refer to White, T. J. et al., Trends Genet., 1989, 5:185), utilizing primers based on the nucleotide sequence of the gene. The asd genes of other microorganisms can be obtained in a similar manner.

Also, the aspC gene of *E. coli* has already been elucidated (nucleotide positions 983742 to 984932, GenBank accession no. NC_000913.1, gi:16128895), and can be obtained by PCR. The aspC genes of other microorganisms can be obtained in a similar manner.

L-lysine-producing bacteria

Examples of L-lysine-producing bacteria belonging to the genus *Escherichia* include mutants having resistance to an L-lysine analogue. The L-lysine analogue inhibits growth of bacteria belonging to the genus *Escherichia*, but this inhibition is fully or partially desensitized when L-lysine is present in a medium. Examples of the L-lysine analogue include, but are not limited to, oxalysine, lysine hydroxamate, S-(2-aminoethyl)-L-cysteine (AEC), γ-methyllysine, α-chlorocaprolactam, and so forth. Mutants having resistance to these lysine analogues can be obtained by subjecting bacteria belonging to the genus *Escherichia* to a conventional artificial mutagenesis treatment. Specific examples of bacterial strains useful for producing L-lysine include *Escherichia coli* AJ11442 (FERM BP-1543, NRRL B-12185; see U.S. Pat. No. 4,346,170) and *Escherichia coli* VL611. In these microorganisms, feedback inhibition of aspartokinase by L-lysine is desensitized.

The strain WC196 may be used as an L-lysine producing bacterium of *Escherichia coli*. This bacterial strain was bred by conferring the AEC resistance to strain W3110, which was derived from *Escherichia coli* K-12. The resulting strain was designated *Escherichia coli* AJ13069 and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, it was converted to an international deposit under the provisions of the Budapest Treaty on Sep. 29, 1995, and received an accession number of FERM BP-5252 (U.S. Pat. No. 5,827,698).

Examples of parent strains which can be used for deriving the L-lysine-producing bacteria of the present invention also include strains in which expression of one or more genes encoding an L-lysine biosynthetic enzyme are enhanced. Examples of the enzymes involved in L-lysine biosynthesis include, but are not limited to, dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyrvate carboxylase (ppc), aspartate semialdehyde dehydrogenease (asd), nicotinamide adenine dinucleotide transhydrogenase (pntAB), and aspartase (aspA) (EP 1253195 A).

Examples of parent strains which can be used for deriving the L-lysine-producing bacteria of the present invention also include strains having decreased or eliminated activity of an enzyme that catalyzes a reaction for generating a compound other than L-lysine by branching off from the biosynthetic pathway of L-lysine. Examples of the enzymes that catalyze a reaction for generating a compound other than L-lysine by branching off from the biosynthetic pathway of L-lysine include homoserine dehydrogenase and lysine decarboxylase (U.S. Pat. No. 5,827,698).

L-cysteine-producing bacteria

Examples of parent strains which can be used for deriving the L-cysteine-producing bacteria of the present invention include, but are not limited to, strains belonging to the genus *Escherichia*, such as *E. coli* JM 15, which is transformed with different cysE alleles encoding feedback-resistant serine acetyltransferases (U.S. Pat. No. 6,218,168, Russian patent application 2003121601); *E. coli* W3110 having over-expressed genes which encode proteins suitable for secreting substances toxic for cells (U.S. Pat. No. 5,972,663); *E. coli* strains having lowered cysteine desulfohydrase activity (JP 11-155571A); *E. coli* W3110 with increased activity of a positive transcriptional regulator for cysteine regulon encoded by the cysB gene (WO0127307A1), and the like.

L-leucine-producing bacteria

Examples of parent strains which can be used for deriving the L-leucine-producing bacteria of the present invention include, but are not limited to, strains belonging to the genus *Escherichia*, such as *E. coli* strains resistant to leucine analogs, including β-2-thienylalanine, 3-hydroxyleucine, 4-azaleucine, and 5,5,5-trifluoroleucine (JP 62-34397B and JP 08-70879A); *E. coli* strains obtained by the gene-engineering method described in WO96/06926; *E. coli* H-9068 (JP 08-70879A), and the like.

The bacterium of the present invention may be improved by enhancing the expression of one or more genes involved in L-leucine biosynthesis. Examples include genes of the leuABCD operon, which are preferably represented by the mutant leuA gene encoding isopropylmalate synthase freed from feedback inhibition by L-leucine (U.S. Pat. No. 6,403,342). In addition, the bacterium of the present invention may be improved by enhancing the expression of one or more genes encoding proteins which secrete L-amino acid from the bacterial cell. Examples of such genes include the b2682 and b2683 genes (ygaZH genes, EP1239041 A2).

L-histidine-producing bacteria

Examples of parent strains for deriving the L-histidine-producing bacteria of the present invention include, but are not limited to, strains belonging to the genus *Escherichia*, such as *E. coli* strain 24 (VKPM B-5945, RU2003677); *E. coli* strain 80 (VKPM B-7270, RU2119536); *E. coli* NRRL B-12116-B12121 (U.S. Pat. No. 4,388,405); *E. coli* H-9342 (FERM BP-6675) and H-9343 (FERM BP-6676) (U.S. Pat. No. 6,344,347); *E. coli* H-9341 (FERM BP-6674) (EP1085087); *E. coli* A180/pFM201 (U.S. Pat. No. 6,258,554), and the like.

Examples of parent strains which can be used for deriving the L-histidine-producing bacteria of the present invention also include strains in which expression of one or more genes encoding an L-histidine biosynthetic enzyme are enhanced. Examples of the L-histidine-biosynthetic enzymes include ATP phosphoribosyltransferase (hisG), phosphoribosyl AMP cyclohydrolase (hisI), phosphoribosyl-ATP pyrophosphohydrolase (hisIE), phosphoribosyl-formimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the genes encoding the L-histidine biosynthetic enzyme (hisG, hisBHAFI) are inhibited by L-histidine, and therefore an L-histidine-producing ability can also be efficiently enhanced by introducing a mutation conferring resistance to the feedback inhibition into ATP phosphoribosyltransferase (hisG) (Russian Patent Nos. 2003677 and 2119536).

Specific examples of strains having an L-histidine-producing ability include *E. coli* FERM-P 5038 and 5048 in which a vector carrying a DNA encoding an L-histidine-biosynthetic enzyme (JP 56-005099 A) has been introduced, *E.coli* strains into which rht, a gene for an amino acid-export (EP1016710A), has been introduced, *E. coli* 80 strain which has been imparted with sulfaguanidine, DL-1,2,4-triazole-3-alanine, and streptomycin-resistance (VKPM B-7270, Russian Patent No. 2119536), and so forth.

L-glutamic acid-producing bacteria

Examples of parent strains for deriving the L-glutamic acid-producing bacteria of the present invention include, but are not limited to, strains belonging to the genus *Escherichia*, such as *E. coli* VL334thrC$^+$ (EP 1172433). *E. coli* VL334 (VKPM B-1641) is an L-isoleucine and L-threonine auxotrophic strain having mutations in the thrC and ilvA genes (U.S. Pat. No. 4,278,765). A wild-type allele of the thrC gene was transferred by the method of general transduction, using bacteriophage P1 grown on wild-type *E. coli* K12 (VKPM B-7) cells. As a result, an L-isoleucine auxotrophic strain VL334thrC$^+$ (VKPM B-8961) was obtained. This strain is able to produce L-glutamic acid.

Examples of parent strains which can be used for deriving the L-glutamic acid-producing bacteria of the present invention include, but are not limited to, strains in which expression of one or more genes encoding an L-glutamic acid biosynthetic enzyme are enhanced. Examples of the enzymes involved in L-glutamic acid biosynthesis include glutamate dehydrogenase, glutamine synthetase, glutamate synthetase, isocitrate dehydrogenase, aconitate hydratase, citrate synthase, phosphoenolpyruvate carboxylase, pyruvate carboxylase, pyruvate dehydrogenase, pyruvate kinase, phosphoenolpyruvate synthase, enolase, phosphoglyceromutase, phosphoglycerate kinase, glyceraldehyde-3-phophate dehydrogenase, triose phosphate isomerase, fructose bisphosphate aldolase, phosphofructokinase, and glucose phosphate isomerase.

Examples of strains modified so that expression of the citrate synthetase gene, the phosphoenolpyruvate carboxylase gene, and/or the glutamate dehydrogenase gene is/are enhanced include those disclosed in EP1078989A, EP955368A, and EP952221A.

Examples of parent strains which can be used for deriving the the L-glutamic acid-producing bacteria of the present invention also include strains having decreased or eliminated activity of an enzyme that catalyzes synthesis of a compound other than L-glutamic acid, and branching off from an L-glutamic acid biosynthesis pathway. Examples of such enzymes include isocitrate lyase, α-ketoglutarate dehydrogenase, phosphotransacetylase, acetate kinase, acetohydroxy acid synthase, acetolactate synthase, formate acetyltransferase, lactate dehydrogenase, and glutamate decarboxylase. Bacteria belonging to the genus *Echerichia* deficient in α-ketoglutarate dehydrogenase activity or having a reduced α-ketoglutarate dehydrogenase activity and methods for obtaining them are described in U.S. Pat. Nos. 5,378,616 and 5,573,945. Specifically, these strains include the following:

*E. coli* W3110sucA::Kmr
*E. coli* AJ12624 (FERM BP-3853)
*E. coli* AJ12628 (FERM BP-3854)
*E. coli* AJ12949 (FERM BP-4881)

*E. coli* W3110sucA::Kmr is obtained by disrupting the a-ketoglutarate dehydrogenase gene (hereinafter referred to as "sucA gene") of *E. coli* W3110. This strain is completely deficient in α-ketoglutarate dehydrogenase.

Other examples of L-glutamic acid-producing bacteria include mutant strains belonging to the genus *Pantoea* which are deficient in α-ketoglutarate dehydrogenase activity or have a decreased α-ketoglutarate dehydrogenase activity, and can be obtained as described above. Such strains include *Pantoea ananatis* AJ13356. (U.S. Pat. No. 6,331,419). *Pantoea ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 under accession no. FERM P-16645. It was then converted to an international deposit under the provisions of Budapest Treaty on Jan. 11, 1999 and received accession no. FERM BP-6615. *Pantoea ananatis* AJ13356 is deficient in α-ketoglutarate dehydrogenase activity as a result of disruption of the αKGDH-E1 subunit gene (sucA). The above strain was identified as *Enterobacter agglomerans* when it was isolated and deposited as *Enterobacter agglomerans* AJ 13356. However, it was recently re-classified as *Pantoea ananatis* on the basis of nucleotide sequencing of 16S rRNA and so forth. Although AJ13356 was deposited at the aforementioned depository as *Enterobacter agglomerans*, for the purposes of this specification, they are described as *Pantoea ananatis*.

L-phenylalanine-producing bacteria

Examples of parent strains which can be used for deriving the L-phenylalanine-producing bacteria of the present invention include, but are not limited to, strains belonging to the genus *Escherichia*, such as *E. coli* AJ12739 (tyrA::Tn10, tyrR) (VKPM B-8197); *E. coli* HW1089 (ATCC 55371) harboring the pheA34 gene (U.S. Pat. No. 5,354,672); *E. coli* MWEC101-b (KR8903681); *E. coli* NRRL B-12141, NRRL B-12145, NRRL B-12146, and NRRL B-12147 (U.S. Pat. No. 4,407,952). Also, as a parent strain, *E. coli* K-12 [W3110 (tyrA)/pPHAB (FERM BP-3566), *E. coli* K-12 [W3110 (tyrA)/pPHAD] (FERM BP-12659), *E. coli* K-12 [W3110 (tyrA)/pPHATerm] (FERM BP-12662), and *E. coli* K-12 [W3110 (tyrA)/pBR-aroG4, pACMAB] named AJ 12604 (FERM BP-3579) may be used (EP 488424 B1). Furthermore, L-phenylalanine-producing bacteria belonging to the genus *Escherichia* with an enhanced activity of the protein encoded by the yedA gene or the yddG gene may also be used (U.S. patent applications Ser. No. 2003/0148473 A1 and 2003/0157667 A1).

L-tryptophan-producing bacteria

Examples of parent strains which can be used for deriving the L-tryptophan-producing bacteria of the present invention include, but are not limited to, strains belonging to the genus *Escherichia*, such as *E. coli* JP4735/pMU3028 (DSM10122) and JP6015/pMU91 (DSM10123) deficient in tryptophanyl-tRNA synthetase encoded by a mutant trpS gene (U.S. Pat. No. 5,756,345); *E. coli* SV164 (pGH5) having the serA allele encoding phosphoglycerate dehydrogenase free from feedback inhibition by serine and the trpE allele encoding anthranilate synthase free from feedback inhibition by tryptophan (U.S. Pat. No. 6,180,373); *E. coli* AGX17 (pGX44) (NRRL B-12263) and AGX6(pGX50)aroP (NRRL B-12264) deficient in the enzyme tryptophanase (U.S. Pat. No. 4,371,614); *E. coli* AGX17/pGX50,pACKG4-pps in which a phosphoenolpyruvate-producing ability is enhanced (WO9708333, U.S. Pat. No. 6,319,696), and the like may be used.

Previously, it was identified that the yddG gene encodes a membrane protein which is not involved in a biosynthetic pathway of any L-amino acid, and imparts to a microorganism resistance to L-phenylalanine and several amino acid analogues when the wild-type allele of the gene is amplified on a multi-copy vector in the microorganism. Besides, the yddG gene can enhance production of L-phenylalanine or L-tryptophan when additional copies are introduced into the cells of the respective producing strain (WO03044192). So it is desirable that the L-tryptophan-producing bacterium be further modified to have enhanced expression of the yddG open reading frame.

Examples of parent strains which can be used for deriving the L-tryptophan-producing bacteria of the present invention also include strains in which one or more activities of the enzymes selected from anthranilate synthase, phosphoglycerate dehydrogenase, and tryptophan synthase are enhanced. The anthranilate synthase and phosphoglycerate dehydrogenase are both subject to feedback inhibition by L-tryptophan and L-serine, so that a mutation desensitizing the feedback inhibition may be introduced into these enzymes. Specific examples of strains having such a mutation include a *E. coli* SV164 which harbors desensitized anthranilate synthase and a transformant strain obtained by introducing into the *E. coli* SV 164 the plasmid pGH5 (WO 94/08031), which contains a mutant serA gene encoding feedback-desensitized phosphoglycerate dehydrogenase.

Examples of parent strains which can be used for deriving the L-tryptophan-producing bacteria of the present invention also include strains into which the tryptophan operon which contains a gene encoding desensitized anthranilate synthase has been introduced (JP 57-71397 A, JP 62-244382 A, U.S. Pat. No. 4,371,614). Moreover, L-tryptophan-producing ability may be imparted by enhancing expression of a gene which encodes tryptophan synthase, among tryptophan operons (trpBA). The tryptophan synthase consists of α and β subunits which are encoded by trpA and trpB, respectively.

L-proline-producing bacteria

Examples of parent strains which can be used for deriving the L-proline-producing bacteria of the present invention include, but are not limited to, strains belonging to the genus *Escherichia*, such as *E. coli* 702ilvA (VKPM B-8012) which is deficient in the ilvA gene, and is able to produce L-proline (EP 1172433). The bacterium of the present invention may be improved by enhancing the expression of one or more genes involved in L-proline biosynthesis. Examples of such genes for L-proline-producing bacteria include the proB gene encoding glutamate kinase, which has feedback inhibition by L-proline desensitized (DE Patent 3127361). In addition, the bacterium of the present invention may be improved by enhancing the expression of one or more genes encoding proteins excreting L-amino acid from a bacterial cell. Such genes are exemplified by the b2682 and b2683 genes (ygaZH genes) (EP1239041 A2).

Examples of bacteria belonging to the genus *Escherichia*, which have an activity to produce L-proline, include the following *E. coli* strains: NRRL B-1 2403 and NRRL B-12404 (GB Patent 2075056), VKPM B-8012 (Russian patent application 2000124295), plasmid mutants described in DE Patent 3127361, plasmid mutants described by Bloom F. R. et al (The 15$^{th}$ Miami winter symposium, 1983, p.34), and the like.

L-arginine-producing bacteria

Examples of parent strains which can be used for deriving the L-arginine-producing bacteria of the present invention include, but are not limited to, strains belonging to the genus *Escherichia*, such as *E. coli* strain 237 (VKPM B-7925) (U.S. Patent Application 2002/0058315 A1) and its derivative strains harboring mutant N-acetylglutamate synthase (Russian Patent Application No. 2001112869), *E. coli* strain 382 (VKPM B-7926) (EP1170358A1), an arginine-producing strain which has the argA gene encoding N-acetylglutamate synthetase introduced therein (JP 57-5693A), and the like.

Examples of parent strains which can be used for deriving the L-arginine producing bacteria of the present invention also include strains in which expression of one or more genes encoding an L-arginine biosynthetic enzyme are enhanced. Examples of the L-arginine biosynthetic enzymes include N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase. These arginine biosynthetic genes exist on the Arg operon (argCJBDFRGH), and are regulated by an arginine repressor encoded by argR (J Bacteriol. December 2002;184(23):6602-14). Therefore, disruption of the arginine repressor results in an increase in the expression of the Arg operon, thus enhances the activities of the L-arginine-producing enzymes (U.S. patent application Ser. No. 2002/0045223 A1).

2. Method of the present invention

The method of the present invention is a method for producing an L-amino acid comprising cultivating the bacterium of the present invention in a culture medium to produce and excrete the L-amino acid into the medium, and collecting the L-amino acid from the medium.

In the present invention, the cultivation, collection, and purification of L-amino acid from the medium and the like may be performed in a manner similar to conventional fermentation methods wherein an amino acid is produced using a bacterium.

A medium used for culture may be either a synthetic or natural medium, so long as the medium includes a carbon source and a nitrogen source and minerals and, if necessary, appropriate amounts of nutrients which the bacterium requires for growth. The carbon source may include various carbohydrates, such as glucose and sucrose, and various organic acids. Depending on the mode of assimilation of the used microorganism, alcohol, including ethanol and glycerol, may be used. As the nitrogen source, various ammonium salts such as ammonia and ammonium sulfate, other nitrogen compounds such as amines, a natural nitrogen source such as peptone, soybean-hydrolysate, and digested fermentative microorganisms can be used. As minerals, potassium monophosphate, magnesium sulfate, sodium chloride, ferrous sulfate, manganese sulfate, calcium chloride, and the like can be used. As vitamins, thiamine, yeast extract, and the like, can be used.

The cultivation is preferably performed under aerobic conditions, such as a shaking culture, and a stirring culture with aeration, at the temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, 1 to 5-day cultivation leads to accumulation of the target L-amino acid in the liquid medium.

After cultivation, solids, such as cells, can be removed from the liquid medium by centrifugation or membrane filtration, and then the L-amino acid can be collected and purified by ion-exchange, concentration, and/or crystallization methods.

EXAMPLES

The present invention will be more concretely explained below with reference to the following non-limiting Examples.

Example 1

Construction of a Strain with an Inactivated yafA Gene

1. Deletion of the yafA gene

A strain having the yafA gene deleted is constructed by the method initially developed by Datsenko, K. A. and Wanner, B. L. (Proc. Natl. Acad. Sci. USA, 2000, 97(12), 6640-6645) called "Red-driven integration". According to this procedure, the PCR primers yafAL (SEQ ID NO: 3) and yafAR (SEQ ID NO: 4) homologous to both the regions adjacent to the yafA gene and the gene conferring antibiotic resistance, respectively, in the template plasmid are constructed. The plasmid pACYC184 (NBL Gene Sciences Ltd., UK) (GenBank/EMBL accession number X06403) was used as a template in PCR reaction. Conditions for PCR are as follows: denaturation step for 3 min at 95° C.; profile for two first cycles: I min at 95° C., 30 sec at 50° C., 40 sec at 72° C.; profile for the last 25 cycles: 30 sec at 95° C., 30 sec at 72° C.; final step: 5 min at 72° C.

Figure 1:
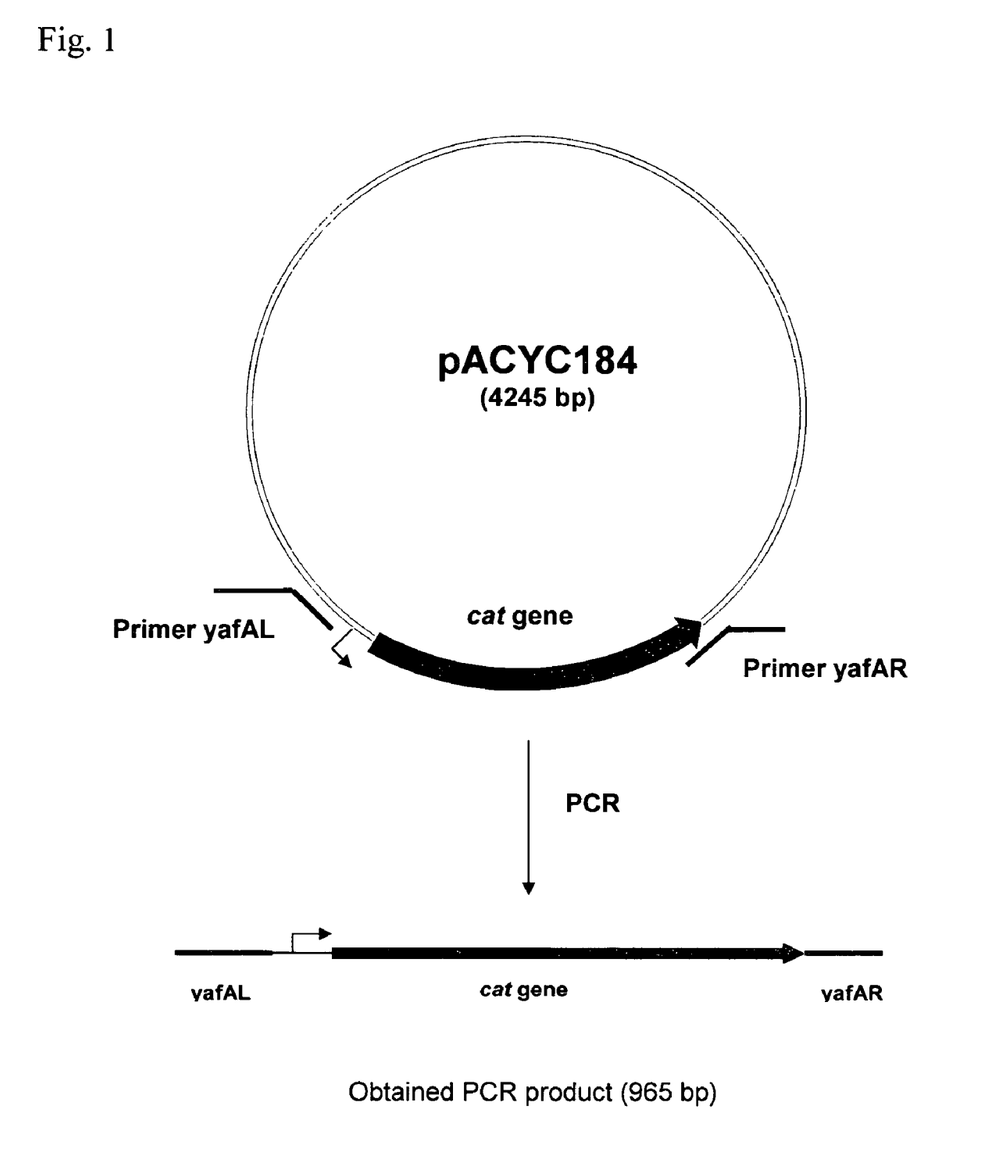
FIG. 1 shows the relative positions of primers yafAL and yafAR on plasmid pACYC184, which is used for amplification of the cat gene.

A 965 bp PCR product (FIG. 1, SEQ ID NO: 5) was obtained and was purified in agarose gel and was used for electroporation of E. coli MG1655 (ATCC 700926), which contains the plasmid pKD46 having temperature-sensitive replication. The plasmid pKD46 (Datsenko, K. A. and Wanner, B. L., Proc. Natl. Acad. Sci. USA, 2000, 97:12: 6640-45) includes a 2,154 nucleotide (31088-33241) DNA fragment of phage λ (GenBank accession No. J02459), and contains genes of the λ Red homologous recombination system (γ, β, exo genes) under control of the arabinose-inducible $P_{araB}$ promoter. The plasmid pKD46 is necessary for integration of the PCR product into the chromosome of strain MG1655.

Electrocompetent cells were prepared as follows: night culture of E. coli MG1655 was grown at 30° C. in LB medium containing ampicillin (100 mg/l), was diluted in 100 times with 5 ml of SOB medium (Sambrook et al, "Molecular Cloning A Laboratory Manual, Second Edition", Cold Spring Harbor Laboratory Press (1989)) containing ampicillin and L-arabinose (1 mM). The obtained culture was grown with aeration at 30° C. to an $OD_{600}$ of ≈0.6 and then made electrocompetent by concentrating 100-fold and washing three times with ice-cold deionized $H_2O$. Electroporation was performed using 70 μl of cells and ≈100 ng of PCR product. Cells after electroporation were incubated with 1 ml of SOC medium (Sambrook et al, "Molecular Cloning A Laboratory Manual, Second Edition", Cold Spring Harbor Laboratory Press (1989)) at 37° C. for 2.5 h and after that plated onto L-agar to be grown at 37° C. to select $Cm^R$ recombinants. Then, to eliminate the pKD46 plasmid, 2 passages on L-agar with Cm at 42° C. were performed and the obtained colonies were tested for sensitivity to ampicillin.

2. Verification of the yafA gene deletion by PCR

Figure 2:
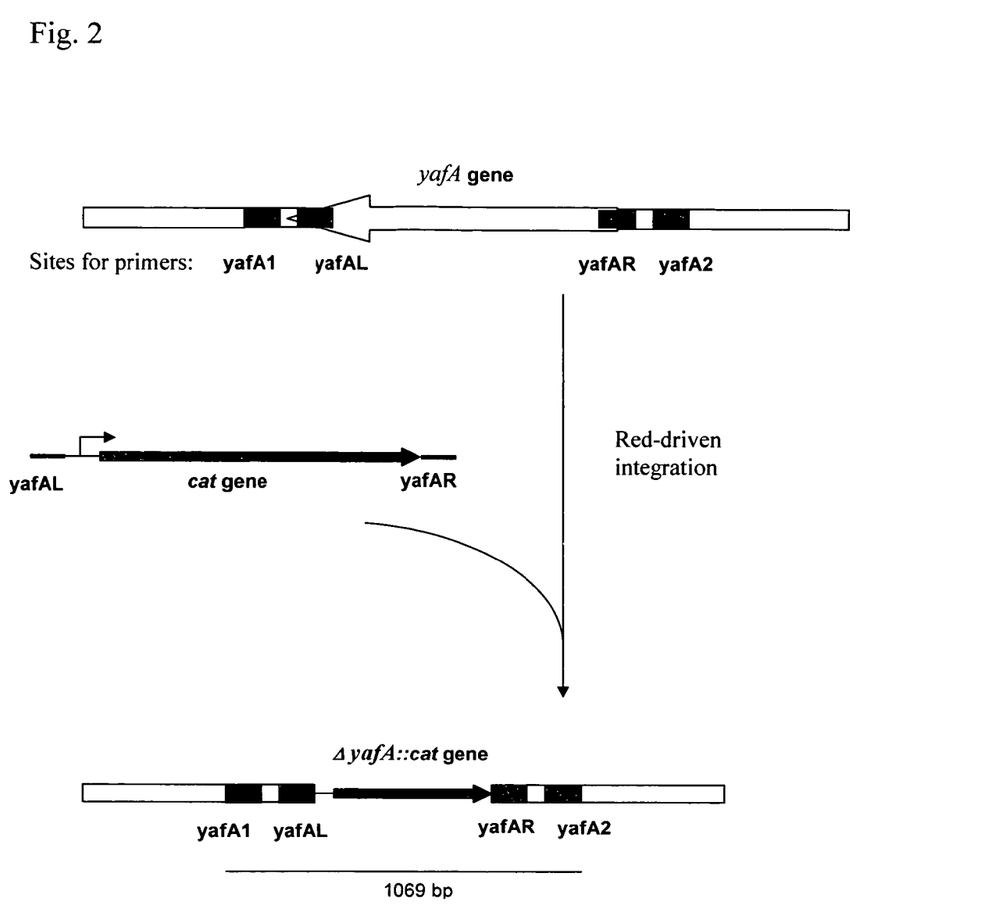
FIG. 2 shows the construction of the chromosomal DNA fragment comprising the inactivated yafA gene.

The mutant having the yafA gene deleted and marked with Cm resistance gene was verified by PCR. Locus-specific primers yafA1 (SEQ ID NO: 6) and yafA2 (SEQ ID NO: 7) were used in PCR for the verification. Conditions for PCR verification were as follows: denaturation step for 3 min at 94° C.; profile for the 30 cycles: 30 sec at 94° C., 30 sec at 54° C., 1 min at 72° C.; final step: 7 min at 72° C. The PCR product obtained in the reaction with the cells of parental yafA⁺ MG1655 strain as a template was 1403 bp in length. The PCR product obtained in the reaction with the cells of the strain as a template was 1069 nucleotides in length (FIG. 2). The mutant strain was named MG1655 ΔyafA::cat.

Example 2

Production of L-threonine by E. coli B-3996-ΔyafA

To test the effect of inactivation of the yafA gene on threonine production, DNA fragments from the chromosome of the above-described E. coli MG 1655 ΔyafA::cat were transferred to the threonine-producing E. coli strain VKPM B-3996 by P1 transduction (Miller, J. H. Experiments in Molecular Genetics, Cold Spring Harbor Lab. Press, 1972, Plainview, N.Y.) to obtain the strain B-3996-ΔyafA.

Both E. coli strains, B-3996 and B-3996-ΔyafA, were grown for 18-24 hours at 37° C. on L-agar plates. To obtain a seed culture, the strains were grown on a rotary shaker (250 rpm) at 32° C. for 18 hours in 20×200-mm test tubes containing 2 ml of L-broth supplemented with 4% glucose. Then, the fermentation medium was inoculated with 0.21 ml (10%) of seed material. The fermentation was performed in 2 ml of minimal medium for fermentation in 20×200-mm test tubes. Cells were grown for 65 hours at 32° C. with shaking at 250 rpm.

After cultivation, the amount of L-threonine, which had accumulated in the medium, was determined by paper chromatography using the following mobile phase: butanol-acetic acid-water=4:1:1 (v/v). A solution of ninhydrin (2%) in acetone was used as a visualizing reagent. A spot containing L-threonine was cut off, L-threonine was eluted with 0.5% water solution of $CdCl_2$, and the amount of L-threonine was estimated spectrophotometrically at 540 nm. The results often independent test tube fermentations are shown in Table 1. As follows from Table 1, B-3996-ΔyafA caused accumulation of a higher amount of L-threonine, as compared with B-3996.

The composition of the fermentation medium (g/l) was as follows:

| | |
|---|---|
| Glucose | 80.0 |
| $(NH_4)_2SO_4$ | 22.0 |
| NaCl | 0.8 |
| $KH_2PO_4$ | 2.0 |
| $MgSO_4 \cdot 7H_2O$ | 0.8 |
| $FeSO_4 \cdot 7H_2O$ | 0.02 |
| $MnSO_4 \cdot 5H_2O$ | 0.02 |
| Thiamine HCl | 0.0002 |
| Yeast extract | 1.0 |
| $CaCO_3$ | 30.0 |

Glucose and magnesium sulfate were sterilized separately. $CaCO_3$ was sterilized by dry-heat at 180° C. for 2 hours. The pH was adjusted to 7.0. The antibiotic was introduced into the medium after sterilization.

TABLE 1

| Strain | $OD_{540}$ | Amount of L-threonine, g/l |
|---|---|---|
| B-3996 | 19.6 ± 0.8 | 26.0 ± 1.2 |
| B-3996-ΔyafA | 20.1 ± 0.5 | 27.8 ± 1.0 |

Example 3

Production of L-lysine by *E. coli* AJ11442-ΔyafA

To test the effect of inactivation of the yafA gene on lysine production, DNA fragments from the chromosome of the above-described *E. coli* strain MG1655 ΔyafA::cat can be transferred to the lysine-producing *E. coli* strain WC196 (pCABD2) by P1 transduction (Miller, J. H. Experiments in Molecular Genetics, Cold Spring Harbor Lab. Press, 1972, Plainview, N.Y.) to obtain the strain WC196(pCABD2)-ΔyafA. The pCABD2 plasmid includes the dapA gene encoding dihydrodipicolinate synthase having a mutation which desensitizes feedback inhibition by L-lysine, the lysC gene encoding aspartokinase III having a mutation which desensitizes feedback inhibition by L-lysine, the dapB gene encoding dihydrodipicolinate reductase, and the ddh gene encoding diaminopimelate dehydrogenase, and a streptomycin resistance gene (U.S. Pat. No. 6,040,160).

Both *E. coli* strains, WC196(pCABD2) and WC196 (pCABD2)-ΔyafA can be cultured in L-medium containing streptomycin (20 mg/l) at 37° C. 0.3 ml of the obtained culture can be inoculated into 20 ml of the fermentation medium containing the required drugs in a 500-mi flask. The cultivation can be carried out at 37° C. for 16 h by using a reciprocal shaker at the agitation speed of 115 rpm. After the cultivation, the amounts of L-lysine and residual glucose in the medium can be measured by a known method (Biotech-analyzer AS210 manufactured by Sakura Seiki Co.). Then, the yield of L-lysine can be calculated relative to consumed glucose for each of the strains.

The composition of the fermentation medium (g/l) is as follows:

| | |
|---|---|
| Glucose | 40 |
| $(NH_4)_2SO_4$ | 24 |
| $K_2HPO_4$ | 1.0 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Yeast extract | 2.0 |

The pH is adjusted to 7.0 by KOH and the medium is autoclaved at 115° C. for 10 min. Glucose and $MgSO_4 \cdot 7H_2O$ are sterilized separately. $CaCO_3$ is dry-heat sterilized at 180° C. for 2 hours and added to the medium for a final concentration of 30 g/l.

Example 4

Production of L-cysteine by *E. coli* JM15(ydeD)-ΔyafA

To test the effect of inactivation of the yafA gene on L-cysteine production, DNA fragments from the chromosome of the above-described *E. coli* MG 1655 ΔyafA::cat can be transferred to the *E. coli* L-cysteine-producing strain JM15(ydeD) by P1 transduction (Miller, J. H. Experiments in Molecular Genetics, Cold Spring Harbor Lab. Press, 1972, Plainview, N.Y.) to obtain the strain JM15(ydeD)-ΔyafA.

*E. coli* JM15(ydeD) is aderivative of *E. coli* JM15 (U.S. Pat. No. 6,218,168), which can be transformed with DNA having the ydeD gene encoding a membrane protein, and is not involved in a biosynthetic pathway of any L-amino acid (U.S. Pat. No. 5,972,663).

Fermentation conditions for evaluation of L-cysteine production were described in detail in Example 6 of U.S. Pat. No. 6,218,168.

Example 5

Production of L-leucine by *E. coli* 57-ΔyafA

To test the effect of inactivation of the yafA gene on L-leucine production, DNA fragments from the chromosome of the above-described *E. coli* strain MG1655 ΔyafA:: cat can be transferred to the *E. coli* L-leucine-producing strain 57 (VKPM B-7386, U.S. Pat. No. 6,124,121) by P1 transduction (Miller, J. H. Experiments in Molecular Genetics, Cold Spring Harbor Lab. Press, 1972, Plainview, N.Y.) to obtain the 57-pMW-ΔyafA strain.

Both *E. coli* strains, 57 and 57-ΔyafA, can be cultured for 18-24 hours at 37° C. on L-agar plates. To obtain a seed culture, the strains can be grown on a rotary shaker (250 rpm) at 32° C. for 18 hours in 20×200-mm test tubes containing 2 ml of L-broth supplemented with 4% sucrose. Then, the fermentation medium can be inoculated with 0.21 ml of seed material (10%). The fermentation can be performed in 2 ml of a minimal fermentation medium in 20×200-mm test tubes. Cells can be grown for 48-72 hours at 32° C. with shaking at 250 rpm. The amount of L-leucine can be measured by paper chromatography (liquid phase composition: butanol-acetic acid-water=4:1:1).

The composition of the fermentation medium (g/l) (pH 7.2) is as follows:

| | |
|---|---|
| Glucose | 60.0 |
| $(NH_4)_2SO_4$ | 25.0 |
| $K_2HPO_4$ | 2.0 |
| $MgSO_4 \cdot 7H_2O$ | 1.0 |
| Thiamine | 0.01 |
| $CaCO_3$ | 25.0 |

Glucose and $CaCO_3$ are sterilized separately.

Example 6

Production of L-histidine by E. coli 80-ΔyafA

To test the effect of inactivation of the yafA gene on L-histidine production, DNA fragments from the chromosome of the above-described E. coli MG1655 ΔyafA::cat can be transferred to the histidine-producing E. coli strain 80 by P1 transduction (Miller, J. H. Experiments in Molecular Genetics, Cold Spring Harbor Lab. Press, 1972, Plainview, N.Y.) to obtain the strain 80-ΔyafA. The strain 80 has been described in Russian patent 2119536 and deposited in the Russian National Collection of Industrial Microorganisms (Russia, 117545 Moscow, 1 st Dorozhny proezd, 1) under accession no. VKPM B-7270.

Both E. coli strains, 80 and 80-ΔyafA can be cultured in L-broth for 6 h at 29° C. Then, 0.1 ml of obtained culture can be inoculated into 2 ml of fermentation medium in a 20×200-mm test tube and cultivated for 65 hours at 29° C. with shaking on a rotary shaker (350 rpm). After cultivation, the amount of histidine which accumulates in the medium can be determined by paper chromatography. The paper can be developed with a mobile phase consisting of n-butanol: acetic acid:water=4:1:1 (v/v). A solution of ninhydrin (0.5%) in acetone can be used as a visualizing reagent.

The composition of the fermentation medium (g/l) (pH 6.0) is as follows:

| | |
|---|---|
| Glucose | 100.0 |
| Mameno (soybean hydrolysate) | 0.2 as total nitrogen |
| L-proline | 1.0 |
| $(NH_4)_2SO_4$ | 25.0 |
| $KH_2PO_4$ | 2.0 |
| $MgSO_4\ 7H_2O$ | 1.0 |
| $FeSO_4\ 7H_2O$ | 0.01 |
| $MnSO_4$ | 0.01 |
| Thiamine | 0.001 |
| Betaine | 2.0 |
| $CaCO_3$ | 60.0 |

Glucose, proline, betaine and $CaCO_3$ are sterilized separately. The pH is adjusted to 6.0 before sterilization.

Example 7

Production of L-glutamate by E. coli VL334thrC+-ΔyafA

To test the effect of inactivation of the yafA gene on L-glutamate production, DNA fragments from the chromosome of the above-described E. coli strain MG1655 ΔyafA:: cat can be transferred to the E. coli L-glutamate-producing strain VL334thrC+ (EP 1172433) by P1 transduction (Miller, J. H. Experiments in Molecular Genetics, Cold Spring Harbor Lab. Press, 1972, Plainview, N.Y.) to obtain the strain VL334thrC+-ΔyafA.

Both strains, VL334thrC+ and VL334thrC+-ΔyafA can be grown for 18-24 hours at 37° C. on L-agar plates. Then, one loop of the cells can be transferred into test tubes containing 2 ml of fermentation medium. The fermentation medium contains glucose (60 g/l), ammonium sulfate (25 g/l), $KH_2PO_4$ (2 g/l), $MgSO_4$ (1 g/l), thiamine (0.1 mg/ml), L-isoleucine (70 μg/ml), and chalk (25 g/l). The pH is adjusted to 7.2. Glucose and chalk are sterilized separately. Cultivation can be carried out at 30° C. for 3 days with shaking. After the cultivation, the amount of L-glutamic acid which is produced can be determined by paper chromatography (liquid phase composition of butanol-acetic acid-water=4:1:1) with subsequent staining by ninhydrin (1% solution in acetone) and further elution of the compounds in 50% ethanol with 0.5% $CdCl_2$.

Example 8

Production of L-phenylalanine by E. coli AJ12739-ΔyafA

To test the effect of inactivation of the yafA gene on L-phenylalanine production, DNA fragments from the chromosome of the above-described E. coli MG1655 ΔyafA::cat can be transferred to the phenylalanine-producing E. coli strain AJ12739 by P1 transduction (Miller, J. H. Experiments in Molecular Genetics, Cold Spring Harbor Lab. Press, 1972, Plainview, N.Y.) to obtain the strain AJ12739-ΔyafA. The strain AJ12739 has been deposited in the Russian National Collection of Industrial Microorganisms (VKPM) (Russia, 117545 Moscow, $1^{st}$ Dorozhny proezd, 1) on Nov. 6, 2001 under accession no. VKPM B-8197.

Both strains, AJ12739-ΔyafA and AJ12739 can be cultivated at 37° C. for 18 hours in a nutrient broth. 0.3 ml of the obtained cultures can each be inoculated into 3 ml of fermentation medium in a 20×200-mm test tube and cultivated at 37° C. for 48 hours with shaking on a rotary shaker. After cultivation, the amount of phenylalanine which accumulates in the medium can be determined by TLC. The 10×15-cm TLC plates coated with 0.11-mm layers of Sorbfil silica gel containing no fluorescent indicator (Stock Company Sorbpolymer, Krasnodar, Russia) can be used. The Sorbfil plates can be developed with a mobile phase consisting of propan-2-ol: ethylacetate: 25% aqueous ammonia: water=40:40:7:16 (v/v). A solution of ninhydrin (2%) in acetone can be used as a visualizing reagent.

The composition of the fermentation medium (g/l) is as follows:

| | |
|---|---|
| Glucose | 40.0 |
| $(NH_4)_2SO_4$ | 16.0 |
| $K_2HPO_4$ | 0.1 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Thiamine HCl | 0.0002 |
| Yeast extract | 2.0 |
| Tyrosine | 0.125 |
| $CaCO_3$ | 20.0 |

Glucose and magnesium sulfate are sterilized separately. CaCO$_3$ is dry-heat sterilized at 180° C. for 2 hours. The pH is adjusted to 7.0.

Example 9

Production of L-tryptophan by *E. coli* SV 164 (pGH5)-ΔyafA

To test the effect of inactivation of the yafA gene on L-tryptophan production, DNA fragments from the chromosome of the above-described *E. coli* strain MG 1655 ΔyafA::cat was transferred to the tryptophan-producing *E. coli* strain SV 164 (pGH5) by P1 transduction (Miller, J. H. Experiments in Molecular Genetics, Cold Spring Harbor Lab. Press, 1972, Plainview, N.Y.) to obtain the strain SV164 (pGH5)-ΔyafA. The strain SV164 has the trpE allele encoding anthranilate synthase free from feedback inhibition by tryptophan. The plasmid pGH5 harbors a mutant serA gene encoding phosphoglycerate dehydrogenase free from feedback inhibition by serine. The strain SV164 (pGH5) was described in detail in U.S. Pat. No. 6,180,373 or EP 0662143.

Both strains, SV164(pGH5)-ΔyafA and SV164(pGH5), were cultivated with shaking at 37° C. for 18 hours in 3 ml of nutrient broth supplemented with tetracycline (5 μg/ml, marker of pGH5 plasmid). The obtained cultures (0.3 ml each) were inoculated into 3 ml of a fermentation medium containing tetracycline (5 μg/ml) in 20×200-mm test tubes, and cultivated at 37° C. for 72 hours with a rotary shaker at 250 rpm. After cultivation, the amount of tryptophan which accumulated in the medium was determined by TLC as described in Example 8. The fermentation medium components are listed in Table 2, and are sterilized in separate groups (A, B, C, D, E, F, and H) to avoid adverse interactions during sterilization. The results of eight independent test tube fermentations are shown in Table 3. As follows from Table 3, SV164(pGH5)-ΔyafA caused accumulation of a higher amount of L-tryptophan, as compared with SV164 (pGH5).

TABLE 2

| Groups | Component | Final concentration, g/l |
|---|---|---|
| A | KH$_2$PO$_4$ | 1.5 |
|   | NaCl | 0.5 |
|   | (NH$_4$)$_2$SO$_4$ | 1.5 |
|   | L-Methionine | 0.05 |
|   | L-Phenylalanine | 0.1 |
|   | L-Tyrosine | 0.1 |
|   | Mameno (total N) | 0.07 |
| B | Glucose | 40.0 |
|   | MgSO$_4$•7H$_2$O | 0.3 |
| C | CaCl$_2$ | 0.011 |
| D | FeSO$_4$•7H$_2$O | 0.075 |
|   | Sodium citrate | 1.0 |
| E | Na$_2$MoO$_4$•2H$_2$O | 0.00015 |
|   | H$_3$BO$_3$ | 0.0025 |
|   | CoCl$_2$•6H$_2$O | 0.00007 |
|   | CuSO$_4$•5H$_2$O | 0.00025 |
|   | MnCl$_2$•4H$_2$O | 0.0016 |
|   | ZnSO$_4$•H$_2$O | 0.0003 |
| F | Thiamine HCl | 0.005 |
| G | CaCO$_3$ | 30.0 |
| H | Pyridoxine | 0.03 |

The pH of solution A is adjusted to 7.1 with NH$_4$OH.

TABLE 3

| Strain | OD$_{540}$ | Amount of L-tryptophan, g/l |
|---|---|---|
| SV164(pGH5) | 8.4 ± 0.2 | 4.4 ± 0.1 |
| SV164(pGH5)-ΔyafA | 7.7 ± 0.4 | 4.8 ± 0.5 |

Example 10

Production of L-proline by *E. coli* 702ilvA-ΔyafA

To test the effect of inactivation of the yafA gene on L-proline production, DNA fragments from the chromosome of the above-described *E. coli* strain MG1655 ΔyafA::cat can be transferred to the proline-producing *E. coli* strain 702ilvA by P1 transduction (Miller, J. H. Experiments in Molecular Genetics, Cold Spring Harbor Lab. Press, 1972, Plainview, N.Y.) to obtain the strain 702ilvA-ΔyafA. The strain 702ilvA has been deposited in the Russian National Collection of Industrial Microorganisms (VKPM) (Russia, 117545 Moscow, 1$^{st}$ Dorozhny proezd, 1) under accession no. VKPM B-8012.

Both *E. coli* strains, 702ilvA and 702ilvA-ΔyafA can be grown for 18-24 hours at 37° C. on L-agar plates. Then, these strains can be cultivated under the same conditions as in Example 8.

Example 11

Production of L-arginine by *E. coli* 382-ΔyafA

To test the effect of inactivation of the yafA gene on L-arginine production, DNA fragments from the chromosome of the above-described *E. coli* strain MG1655 ΔyafA::cat can be transferred to the arginine-producing *E. coli* strain 382 by P1 transduction (Miller, J. H. Experiments in Molecular Genetics, Cold Spring Harbor Lab. Press, 1972, Plainview, N.Y.) to obtain the strain 382-ΔyafA. The strain 382 has been deposited in the Russian National Collection of Industrial Microorganisms (VKPM) (Russia, 117545 Moscow, 1$^{st}$ Dorozhny proezd, 1) on Apr. 10, 2000 under accession no. VKPM B-7926.

Both strains, 382-ΔyafA and 382, can be cultivated with shaking at 37° C. for 18 hours in 3 ml of nutrient broth. The obtained cultures (0.3 ml each) can be inoculated into 3 ml of a fermentation medium in 20×200-mm test tubes and cultivated at 32° C. for 48 hours on a rotary shaker.

After the cultivation, the amount of L-arginine which had accumulated in the medium can be determined by paper chromatography using the following mobile phase:butanol: acetic acid:water=4:1:1 (v/v). A solution of ninhydrin (2%) in acetone can be used as a visualizing reagent. A spot containing L-arginine can be cut off, L-arginine can be eluted with 0.5% water solution of CdCl$_2$, and the amount of L-arginine can be estimated spectrophotometrically at 540 nm.

The composition of the fermentation medium (g/l) is as follows:

| Glucose | 48.0 |
|---|---|
| (NH$_4$)$_2$SO$_4$ | 35.0 |
| KH$_2$PO$_4$ | 2.0 |
| MgSO$_4$•7H$_2$O | 1.0 |
| Thiamine HCl | 0.0002 |
| Yeast extract | 1.0 |
| L-isoleucine | 0.1 |
| CaCO$_3$ | 5.0 |

Glucose and magnesium sulfate are sterilized separately. CaCO$_3$ is dry-heat sterilized at 180° C. for 2 hours. The pH is adjusted to 7.0.

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

INDUSTRIAL APPLICABILITY

According to the present invention, production of L-amino acids, such as L-threonine, L-lysine, L-cysteine, L-leucine, L-histidine, L-glutamic acid, L-phenylalanine, L-tryptophan, L-proline, and L-arginine of a bacterium of the *Enterobacteriaceae* family can be enhanced.

What is claimed is:

1. A method for producing an L-amino acid selected from the group consisting of L-threonine and L-tryptophan comprising:
cultivating an *Escherichia coli* bacterium in a medium so to produce and excrete said L-amino acid into the medium, and
collecting said L-amino acid from the medium, wherein said bacterium has been modified to attenuate expression of the yafA gene, and wherein said yafA gene encodes a protein which is at least 95% homologous to the entire amino acid sequence of SEQ ID NO: 2 and has FrsA regulator activity.

2. The method according to claim 1, wherein said expression of the yafA gene is attenuated by inactivation of the yafA gene.

* * * * *

SEQUENCE LISTING

```
<160> NUMBER OF SEQ ID NOS: 7

<210> SEQ ID NO 1
<211> LENGTH: 1245
<212> TYPE: DNA
<213> ORGANISM: Escherichia coli
<220> FEATURE:
<221> NAME/KEY: CDS
<222> LOCATION: (1)..(1245)

<400> SEQUENCE: 1 atg aca cag gca aac ctg agc gaa acc ctg ttc aaa ccc cgc ttt aaa      48
Met Thr Gln Ala Asn Leu Ser Glu Thr Leu Phe Lys Pro Arg Phe Lys
1               5                   10                  15 cat cct gaa acc tcg acg cta gtc cgc cgc ttt aat cac ggc gca caa      96
His Pro Glu Thr Ser Thr Leu Val Arg Arg Phe Asn His Gly Ala Gln
                20                  25                  30 ccg cct gtg cag tcg gcc ctt gat ggt aaa acc atc cct cac tgg tat     144
Pro Pro Val Gln Ser Ala Leu Asp Gly Lys Thr Ile Pro His Trp Tyr
            35                  40                  45 cgc atg att aac cgt ctg atg tgg atc tgg cgc ggc att gac cca cgc     192
Arg Met Ile Asn Arg Leu Met Trp Ile Trp Arg Gly Ile Asp Pro Arg
        50                  55                  60 gaa atc ctc gac gtc cag gca cgt att gtg atg agc gat gcc gaa cgt     240
Glu Ile Leu Asp Val Gln Ala Arg Ile Val Met Ser Asp Ala Glu Arg
65                  70                  75                  80 acc gac gat gat tta tac gat acg gtg att ggc tac cgt ggc ggc aac     288
Thr Asp Asp Asp Leu Tyr Asp Thr Val Ile Gly Tyr Arg Gly Gly Asn
                85                  90                  95 tgg att tat gag tgg gcc acc cag gcg atg gtg tgg caa caa aaa gcc     336
Trp Ile Tyr Glu Trp Ala Thr Gln Ala Met Val Trp Gln Gln Lys Ala
            100                 105                 110 tgt gcg gaa gac gat ccg caa ctc agt ggt cgt cac tgg ctg cat gcg     384
Cys Ala Glu Asp Asp Pro Gln Leu Ser Gly Arg His Trp Leu His Ala
        115                 120                 125 gct acg ttg tac aac att gcc gcc tat cct cat ctg aaa gga gat gac     432
Ala Thr Leu Tyr Asn Ile Ala Ala Tyr Pro His Leu Lys Gly Asp Asp
    130                 135                 140 ctg gcc gag caa gcg cag gct ttg tca aac cgc gcc tat gaa gag gcc     480
Leu Ala Glu Gln Ala Gln Ala Leu Ser Asn Arg Ala Tyr Glu Glu Ala
145                 150                 155                 160 gct cag cgt cta ccg ggc acg atg cgg cag atg gag ttt acc gta ccc     528
Ala Gln Arg Leu Pro Gly Thr Met Arg Gln Met Glu Phe Thr Val Pro
                165                 170                 175 ggc ggt gcg ccc atc acc ggc ttt ttg cat atg ccg aaa ggc gat ggc     576
Gly Gly Ala Pro Ile Thr Gly Phe Leu His Met Pro Lys Gly Asp Gly
            180                 185                 190 ccg ttc ccg acg gta tta atg tgt ggt ggt ctg gat gcg atg cag acg     624
Pro Phe Pro Thr Val Leu Met Cys Gly Gly Leu Asp Ala Met Gln Thr
        195                 200                 205
```

```
gac tat tac agc ctg tat gaa cgt tat ttt gcg ccg cgc ggc att gcg       672
Asp Tyr Tyr Ser Leu Tyr Glu Arg Tyr Phe Ala Pro Arg Gly Ile Ala
210                 215                 220 atg ctg act att gat atg ccg tcg gtg ggc ttt tct tca aaa tgg aag       720
Met Leu Thr Ile Asp Met Pro Ser Val Gly Phe Ser Ser Lys Trp Lys
225                 230                 235                 240 ctc acc cag gac tcc agc ctg ttg cat cag cac gtc tta aag gcg ctg       768
Leu Thr Gln Asp Ser Ser Leu Leu His Gln His Val Leu Lys Ala Leu
                245                 250                 255 cct aac gta ccg tgg gtg gat cac act cgc gtc gcg gcc ttt ggt ttc       816
Pro Asn Val Pro Trp Val Asp His Thr Arg Val Ala Ala Phe Gly Phe
            260                 265                 270 cgt ttc ggc gct aac gtt gcc gtg cgt ctg gca tac ctt gaa tcg ccg       864
Arg Phe Gly Ala Asn Val Ala Val Arg Leu Ala Tyr Leu Glu Ser Pro
        275                 280                 285 cgt ctg aaa gcg gtt gcc tgt ctt ggt ccg gta gtt cat acc ctg ttg       912
Arg Leu Lys Ala Val Ala Cys Leu Gly Pro Val Val His Thr Leu Leu
    290                 295                 300 agt gat ttt aag tgc cag caa cag gtg ccg gaa atg tat ctt gac gtt       960
Ser Asp Phe Lys Cys Gln Gln Gln Val Pro Glu Met Tyr Leu Asp Val
305                 310                 315                 320 ctg gcc agt cgt ttg ggg atg cat gat gct tcc gat gaa gcg ttg cgc      1008
Leu Ala Ser Arg Leu Gly Met His Asp Ala Ser Asp Glu Ala Leu Arg
                325                 330                 335 gtg gag ctg aat cgc tat tca tta aaa gtg caa gga ttg ctg gga cgt      1056
Val Glu Leu Asn Arg Tyr Ser Leu Lys Val Gln Gly Leu Leu Gly Arg
            340                 345                 350 cgc tgc cca acg cca atg tta tca ggc tac tgg aag aac gat ccg ttc      1104
Arg Cys Pro Thr Pro Met Leu Ser Gly Tyr Trp Lys Asn Asp Pro Phe
        355                 360                 365 agc ccg gaa gag gac tca cgc tta atc acc tca tca tct gct gac ggt      1152
Ser Pro Glu Glu Asp Ser Arg Leu Ile Thr Ser Ser Ser Ala Asp Gly
    370                 375                 380 aaa tta tta gag atc cca ttt aac ccg gtg tat cgg aat ttt gac aaa      1200
Lys Leu Leu Glu Ile Pro Phe Asn Pro Val Tyr Arg Asn Phe Asp Lys
385                 390                 395                 400 ggt ctt cag gaa atc acc gac tgg atc gaa aaa cgc ttg tgt taa          1245
Gly Leu Gln Glu Ile Thr Asp Trp Ile Glu Lys Arg Leu Cys
                405                 410

<210> SEQ ID NO 2
<211> LENGTH: 414
<212> TYPE: PRT
<213> ORGANISM: Escherichia coli

<400> SEQUENCE: 2

Met Thr Gln Ala Asn Leu Ser Glu Thr Leu Phe Lys Pro Arg Phe Lys
1               5                   10                  15

His Pro Glu Thr Ser Thr Leu Val Arg Arg Phe Asn His Gly Ala Gln
                20                  25                  30

Pro Pro Val Gln Ser Ala Leu Asp Gly Lys Thr Ile Pro His Trp Tyr
            35                  40                  45

Arg Met Ile Asn Arg Leu Met Trp Ile Trp Arg Gly Ile Asp Pro Arg
        50                  55                  60

Glu Ile Leu Asp Val Gln Ala Arg Ile Val Met Ser Asp Ala Glu Arg
65                  70                  75                  80

Thr Asp Asp Asp Leu Tyr Asp Thr Val Ile Gly Tyr Arg Gly Gly Asn
                85                  90                  95

Trp Ile Tyr Glu Trp Ala Thr Gln Ala Met Val Trp Gln Gln Lys Ala
```

```
                    100                 105                 110
Cys Ala Glu Asp Asp Pro Gln Leu Ser Gly Arg His Trp Leu His Ala
            115                 120                 125

Ala Thr Leu Tyr Asn Ile Ala Ala Tyr Pro His Leu Lys Gly Asp Asp
        130                 135                 140

Leu Ala Glu Gln Ala Gln Ala Leu Ser Asn Arg Ala Tyr Glu Glu Ala
145                 150                 155                 160

Ala Gln Arg Leu Pro Gly Thr Met Arg Gln Met Glu Phe Thr Val Pro
                165                 170                 175

Gly Gly Ala Pro Ile Thr Gly Phe Leu His Met Pro Lys Gly Asp Gly
            180                 185                 190

Pro Phe Pro Thr Val Leu Met Cys Gly Gly Leu Asp Ala Met Gln Thr
        195                 200                 205

Asp Tyr Tyr Ser Leu Tyr Glu Arg Tyr Phe Ala Pro Arg Gly Ile Ala
    210                 215                 220

Met Leu Thr Ile Asp Met Pro Ser Val Gly Phe Ser Ser Lys Trp Lys
225                 230                 235                 240

Leu Thr Gln Asp Ser Ser Leu Leu His Gln His Val Leu Lys Ala Leu
                245                 250                 255

Pro Asn Val Pro Trp Val Asp His Thr Arg Val Ala Ala Phe Gly Phe
            260                 265                 270

Arg Phe Gly Ala Asn Val Ala Val Arg Leu Ala Tyr Leu Glu Ser Pro
        275                 280                 285

Arg Leu Lys Ala Val Ala Cys Leu Gly Pro Val Val His Thr Leu Leu
    290                 295                 300

Ser Asp Phe Lys Cys Gln Gln Gln Val Pro Glu Met Tyr Leu Asp Val
305                 310                 315                 320

Leu Ala Ser Arg Leu Gly Met His Asp Ala Ser Asp Glu Ala Leu Arg
                325                 330                 335

Val Glu Leu Asn Arg Tyr Ser Leu Lys Val Gln Gly Leu Leu Gly Arg
            340                 345                 350

Arg Cys Pro Thr Pro Met Leu Ser Gly Tyr Trp Lys Asn Asp Pro Phe
        355                 360                 365

Ser Pro Glu Glu Asp Ser Arg Leu Ile Thr Ser Ser Ala Asp Gly
    370                 375                 380

Lys Leu Leu Glu Ile Pro Phe Asn Pro Val Tyr Arg Asn Phe Asp Lys
385                 390                 395                 400

Gly Leu Gln Glu Ile Thr Asp Trp Ile Glu Lys Arg Leu Cys
                405                 410

<210> SEQ ID NO 3
<211> LENGTH: 70
<212> TYPE: DNA
<213> ORGANISM: Artificial Sequence
<220> FEATURE:
<223> OTHER INFORMATION: primer

<400> SEQUENCE: 3
gcgggttaca atagtttcca gtaagtattc tggaggctgc atccatgaca gagaaaaaaa      60
tcactggata                                                            70

<210> SEQ ID NO 4
<211> LENGTH: 70
<212> TYPE: DNA
<213> ORGANISM: Artificial Sequence
<220> FEATURE:
```

<223> OTHER INFORMATION: primer

<400> SEQUENCE: 4
gatttcctga agacctttgt caaaattccg atacaccggg ttaaatggga cgccccgccc    60
tgccactcat    70

<210> SEQ ID NO 5
<211> LENGTH: 965
<212> TYPE: DNA
<213> ORGANISM: Artificial Sequence
<220> FEATURE:
<223> OTHER INFORMATION: Description of Artificial Sequence: cat gene
      flanked by regions for integration

<400> SEQUENCE: 5
gcgggttaca atagtttcca gtaagtattc tggaggctgc atccatgaca cgaataaata    60
cctgtgacgg aagatcactt cgcagaataa ataaatcctg gtgtccctgt tgataccggg   120
aagccctggg ccaacttttg cgaaaatga dacgttgatc ggcacgtaag aggttccaac    180
tttcaccata atgaaataag atcactaccg ggcgtatttt ttgagttatc gagattttca   240
ggagctaagg aagctaaaat ggagaaaaaa atcactggat ataccaccgt tgatatatcc   300
caatggcatc gtaaagaaca ttttgaggca tttcagtcag ttgctcaatg tacctataac   360
cagaccgttc agctggatat tacggccttt ttaaagaccg taaagaaaaa taagcacaag   420
ttttatccgg cctttattca cattcttgcc cgcctgatga atgctcatcc ggaattccgt   480
atggcaatga aagacggtga gctggtgata tgggatagtg ttcacccttg ttacaccgtt   540
ttccatgagc aaactgaaac gttttcatcg ctctggagtg aataccacga cgatttccgg   600
cagtttctac acatatattc gcaagatgtg gcgtgttacg gtgaaaacct ggcctatttc   660
cctaaagggt ttattgagaa tatgttttc gtctcagcca atccctgggt gagtttcacc   720
agttttgatt taaacgtggc caatatggac aacttcttcg cccccgtttt caccatgggc   780
aaatattata cgcaaggcga caaggtgctg atgccgctgg cgattcaggt tcatcatgcc   840
gtctgtgatg cttccatgt cggcagaatg cttaatgaat acaacagta ctgcgatgag    900 tggcagggcg gggcgtccca tttaacccgg tgtatcggaa ttttgacaaa ggtcttcagg   960
aaatc    965

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 6
atctccggtc gctaatcttt tcaa    24

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 7
atctcctgtt gtgatgcaac tgtt    24